US012636187B2

(12) United States Patent
Govari et al.

(10) Patent No.: US 12,636,187 B2
(45) Date of Patent: *May 26, 2026

(54) SURGICAL SYSTEM PRIMING WITH PRESSURE CALIBRATION UTILIZING HANDPIECE ORIENTATION

(71) Applicant: JOHNSON & JOHNSON SURGICAL VISION, INC., Irvine, CA (US)

(72) Inventors: Assaf Govari, Haifa (IL); Vadim Gliner, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 187 days.

This patent is subject to a terminal disclaimer.

(21) Appl. No.: 18/409,183

(22) Filed: Jan. 10, 2024

(65) Prior Publication Data

US 2025/0221852 A1    Jul. 10, 2025

(51) Int. Cl.
*A61F 9/007* (2006.01)
*A61B 34/20* (2016.01)
(Continued)

(52) U.S. Cl.
CPC .......... *A61F 9/00745* (2013.01); *A61B 34/20* (2016.02); *A61B 2017/00725* (2013.01);
(Continued)

(58) Field of Classification Search
CPC ...... A61F 9/007; A61F 9/00745; A61B 34/20; A61B 2017/00725; A61B 2034/2048;
(Continued)

(56) References Cited

U.S. PATENT DOCUMENTS 7,326,183 B2    2/2008    Nazarifar et al.
7,509,831 B2    3/2009    Khashayar
(Continued)

FOREIGN PATENT DOCUMENTS

EP    1550423 B1    12/2008
EP    1896826 B1    9/2013
(Continued)

OTHER PUBLICATIONS

Han et al., "Comparison of Vacuum Rise Time, Vacuum Limit Accuracy, and Occlusion Break Surge of 3 New Phacoemulsification Systems", Journal Cataract and Refractive Surgery, vol. 35, No. 8, pp. 1424-1429, Aug. 1, 2009.
(Continued)

*Primary Examiner* — Vi X Nguyen

(57)    ABSTRACT

A phacoemulsification system and a method are described. The system including: a handpiece having a needle and a sleeve at a distal end and an orientation detection unit; an irrigation module configured to supply irrigation fluid into the eye; an aspiration module configured for aspiring eye fluid; a priming cover for fitting over the distal end of the handpiece during a priming process; external pressure sensors coupled with the priming cover; one or more sensors for monitoring at irrigation and spiration pressure; and a processor configured to operate in a priming process. The priming process includes operating the irrigation module to fill the irrigation channel with fluid and remove air bubbles. The one or more processors are configured for obtaining calibration pressure data from the external pressure sensors and orientation data from the orientation detection unit and for calibrating the sensors of the system in accordance with orientation data.

9 Claims, 5 Drawing Sheets

(51) Int. Cl.
　　*A61B 17/00*　　　　(2006.01)
　　*A61B 90/00*　　　　(2016.01)

(52) U.S. Cl.
　　CPC ． *A61B 2034/2048* (2016.02); *A61B 2090/064*
　　　　(2016.02); *A61B 2217/005* (2013.01); *A61B*
　　　　　　　　　　　　　　　　*2217/007* (2013.01)

(58) Field of Classification Search
　　CPC ........ A61B 2090/064; A61B 2217/005; A61B
　　　　　　　　　　　　　　　　　　　2217/007
　　See application file for complete search history.

(56) References Cited

U.S. PATENT DOCUMENTS

| | | | |
|---|---|---|---|
| 7,644,603 | B2 | 1/2010 | Gordon et al. |
| 7,648,465 | B2 | 1/2010 | Gordon |
| 10,376,328 | B2 | 8/2019 | Charles et al. |
| 10,702,415 | B2 | 7/2020 | Charles |
| 11,317,983 | B2 | 5/2022 | Charles et al. |
| 11,806,465 | B2 | 11/2023 | Govari et al. |
| 2008/0006096 | A1 | 1/2008 | Gordon et al. |
| 2008/0110236 | A1 | 5/2008 | Hajishah et al. |
| 2014/0315174 | A1 | 10/2014 | Sassani et al. |
| 2018/0055592 | A1 | 3/2018 | Charles et al. |
| 2021/0386928 | A1 | 12/2021 | Mehta et al. |
| 2022/0211931 | A1 | 7/2022 | Kuntz et al. |
| 2022/0339034 | A1* | 10/2022 | Govari ............... A61F 9/00736 |
| 2023/0255821 | A1 | 8/2023 | Gliner et al. |
| 2023/0347046 | A1* | 11/2023 | Blanco ................ A61M 5/5086 |
| 2023/0364320 | A1* | 11/2023 | Gliner .................... A61M 1/77 |
| 2025/0186256 | A1 | 6/2025 | Govari et al. |

FOREIGN PATENT DOCUMENTS

| | | |
|---|---|---|
| WO | 2022224076 A1 | 10/2022 |
| WO | 2023152585 A1 | 8/2023 |
| WO | 2023170498 A1 | 9/2023 |

OTHER PUBLICATIONS

Nicoli et al., "Experimental Anterior Chamber 2 Maintenance in Active Versus Passive Phacoemulsification Fluidics Systems", J Cataract Refract Surg, vol. 42, pp. 157-162, 2016.

* cited by examiner

200A

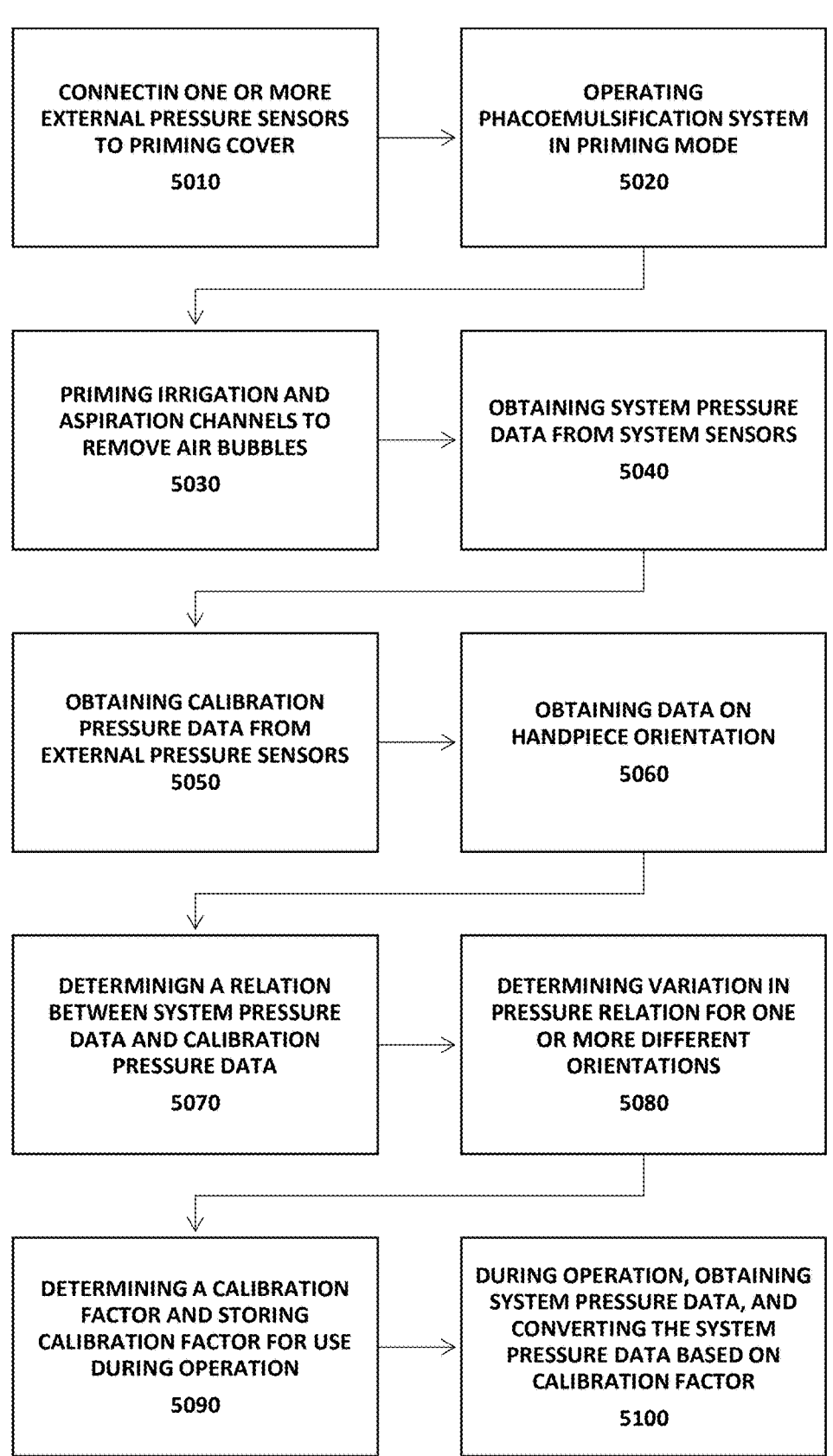

CONNECTIN ONE OR MORE EXTERNAL PRESSURE SENSORS TO PRIMING COVER
5010

OPERATING PHACOEMULSIFICATION SYSTEM IN PRIMING MODE
5020

PRIMING IRRIGATION AND ASPIRATION CHANNELS TO REMOVE AIR BUBBLES
5030

OBTAINING SYSTEM PRESSURE DATA FROM SYSTEM SENSORS
5040

OBTAINING CALIBRATION PRESSURE DATA FROM EXTERNAL PRESSURE SENSORS
5050

OBTAINING DATA ON HANDPIECE ORIENTATION
5060

DETERMINIGN A RELATION BETWEEN SYSTEM PRESSURE DATA AND CALIBRATION PRESSURE DATA
5070

DETERMINING VARIATION IN PRESSURE RELATION FOR ONE OR MORE DIFFERENT ORIENTATIONS
5080

DETERMINING A CALIBRATION FACTOR AND STORING CALIBRATION FACTOR FOR USE DURING OPERATION
5090

DURING OPERATION, OBTAINING SYSTEM PRESSURE DATA, AND CONVERTING THE SYSTEM PRESSURE DATA BASED ON CALIBRATION FACTOR
5100

FIG. 5

SURGICAL SYSTEM PRIMING WITH PRESSURE CALIBRATION UTILIZING HANDPIECE ORIENTATION

TECHNOLOGICAL FIELD

The present disclosure relates to priming of surgical system, and more particularly relates to priming of phacoemulsification system while calibrating pressure of fluid in the system based on orientation of the handpiece of the system.

BACKGROUND#

Phacoemulsification is a surgical procedure used to treat cataracts, which is associated with clouding of the eye's lens and can cause blurred vision, difficulty seeing at night, and sensitivity to light. during the procedure, a surgeon makes a small incision in the patient's cornea and inserts a probe to emit ultrasonic waves breaking the cataract tissue to small pieces. The pieces of the tissue can be suctioned out of the eye, where an artificial lens can be placed.

Typically, prior to surgical operation, the phacoemulsification undergoes priming and/or tuning to prepare the system for required operation. Priming of the system generally involves filling the phacoemulsification system tubing with irrigation fluid (typically balanced salt solution) and creating vacuum in the system.

The priming process is important for ensuring safety and effectiveness of the surgical operation, it helps prevent air bubbles from entering the eye and reduces surgical risks. Generally, the intraocular pressure (IOP) needs to be closely monitored during the phacoemulsification procedure to avoid damage to the patient's eye as a result of vacuum surge or fluid accumulation. To this end phacoemulsification systems typically include sensors monitoring irrigation and vacuum pressures and adjust the pressures to maintain IOP.

Typically, an operator, e.g., physician or nurse, initiating the priming process, is instructed to maintain the handpiece, at a specific position and orientation to ensure accurate flow and pressure measurements during priming.

GENERAL DESCRIPTION

Correspondence between the actual IOP and the readings from the irrigation pressure provided by sensors of the phacoemulsification systems may depend on various factors including distance of the sensors from the tip of the needle, mechanical structure of the handle as well as ambient conditions. This limits the accuracy in determining IOP during the procedure. Accurate pressure and flow data may be crucial for proper surgical operation to eliminate or at least significantly reduce risk of damage to a patient's eye.

As indicated above, priming process generally includes operation of a phacoemulsification system for providing irrigation fluid within respective channels and removing air bubbles from the irrigation channel. During the priming process, the system may also operate to tune one or more sensors thereof, verifying accurate pressure and flow reading during operation. The Present disclosure provides a method and system for priming phacoemulsification systems to enhance accuracy and reproducibility in IOP pressure estimation during the procedure. Due to dimensions of the handpiece of the system, and the various elements implemented therein, such as the needle and sleeve, it is generally difficult to place pressure and/or flow sensors at the tip of the needle or in close proximity thereto. As a result, certain amount of fluid is located within the irrigation channel section between the sensors and the tip of the needle. This certain amount of fluid may vary the pressure reading by the sensor in accordance with orientation of the handpiece. More specifically, the weight of the fluid column that is formed in accordance with orientation of the handpiece may vary the pressure reading and affect pressure calibration.

The present disclosure provides a phacoemulsification system, and a method for use in priming of a phacoemulsification system, utilizing one or more external pressure sensors coupled with or connected to an operation (distal) end of a handpiece of the phacoemulsification system, and at least one orientation detection unit positioned in the handpiece of the phacoemulsification system. The one or more external pressure sensors are used for determining fluid pressure during priming of the system, enabling calibration of one or more internal pressure sensors of the system, and allowing direct and accurate control of irrigation and/or aspiration pressure during surgical operation. The at least one orientation detection unit may comprise one or more accelerometers, one or more gyroscopic sensors or other orientation sensors, and is configured to transmit orientation data to one or more processors of the phacoemulsification system. The use of orientation data enables the one or more processors to further calibrate the pressure in accordance with pressure data collected by the one or more external pressure sensors and data on orientation of the handpiece.

Accordingly, the phacoemulsification system is configured to be operated in a priming mode prior to performing a medical procedure, while allowing various one or more different locations and orientations of the handpiece. For example, a physician or surgeon may hold the handpiece in her hands, practicing or preparing for the coming surgical operation, during priming. The actual location of the handpiece, being in the operator's hands or placed in a selected position, may be flexible, while variation in pressure reading of the one or more sensors of the system due to orientation variation of the handpiece can be compensated for using orientation data received by the at least one orientation detection unit.

Following priming and calibration, the one or more internal sensors are used for monitoring irrigation and/or aspiration pressures during surgical operation.

Additionally, or alternatively, the orientation detection unit may be used to adjust pressure readings during a medical operation such as surgery. This may be used to improve detection of the IOP, while allowing location of the pressure sensor(s) at a selected distance from the distal end of the handpiece. Accordingly, the use of the orientation detection unit may allow simplifying system manufacture and design and may reduce the corresponding costs.

BRIEF DESCRIPTION OF THE DRAWINGS

In order to better understand the subject matter that is disclosed herein and to exemplify how it may be carried out in practice, examples will now be described, by way of non-limiting example only, with reference to the accompanying drawings, in which:

FIG. 3A illustrates horizontal orientation of the handpiece, FIG. 3B illustrates an upward orientation of the handpiece, and FIG. 3C illustrates a downward orientation of the handpiece:

FIG. 5 exemplifies an additional method for use in priming of a phacoemulsification system according to some examples of the present disclosure.

DETAILED DESCRIPTION OF EXAMPLES

Figure 1:
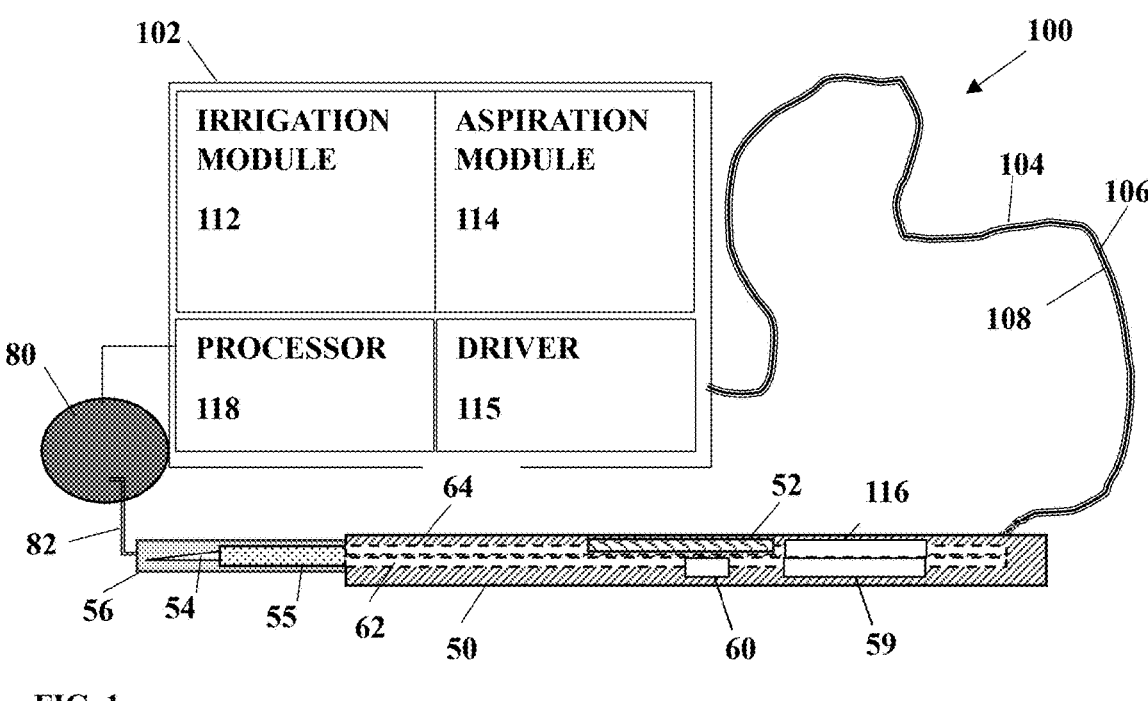
FIG. 1 schematically illustrates a phacoemulsification system utilizing one or more external pressure sensors according to some examples of the present disclosure.

As indicated above, the present disclosure provides a phacoemulsification system utilizing one or more external sensors and at least one orientation unit, and a respective method. The phacoemulsification system is operable for calibrating a pressure sensor during pre-use priming process, while enabling flexible location of a handpiece thereof. Reference is made to FIG. 1 schematically illustrating a phacoemulsification system 100 according to some examples of the present disclosure. System 100 includes a handpiece 50 coupled with unit 102 via connection line 104 configured to provide irrigation, aspiration, and additional functionalities, e.g., power, to handpiece 50. Connection line 104 carries irrigation line 106 and aspiration line 108 to provide connection between irrigation module 112 and aspiration module 114 located in unit 102 and handpiece 50.

Handpiece 50 may include at least one vibrating element 52, e.g., piezoelectric crystal and corresponding circuitry, and a needle 54 and sleeve 55 located at a distal end of handpiece 50. Irrigation channel 62 and aspiration channel 64 go through handpiece 50 from a proximal end to a distal end thereof, and couple needle 54 with aspiration line 108 and couple sleeve 55 with irrigation line 106 to allow flow of fluid and/or material to/from the patient's eye. Additionally, handpiece 50 includes at least one orientation detection unit 60, e.g., formed of one or more accelerometers, gyroscopic unit, or other orientation detection sensors. In some examples, as described above, handpiece 50 may also include one or more internal sensors 116 of phacoemulsification system 100, and an anti-vacuum surge (AVS) module 59. In another example, AVS module 59 may be coupled with an irrigation line 106 and/or an aspiration line 108 anywhere along connection line 104, e.g., proximal to the proximal end of handpiece 50.

Vibrating element 52 is operable for vibrating at a selected frequency to emulsify a lens of a patient's eye during a surgical procedure. Additionally, needle 54 and sleeve 55 may provide a portion of irrigation 62 and aspiration 64 channels to transmit irrigation fluid and to apply aspiration vacuum at the operation site as described in more details below: As indicated above, handpiece 50 may include one or more sensors 116, internal channels associated with aspiration channel 64 and irrigation channel 62 and may also include AVS module 59 configured to block aspiration flow in response to detection an occlusion or an occlusion break. AVS 59 may be coupled with or connected to sensor(s) 116 for receiving data on pressure and/or flow rate in irrigation 62 and/or aspiration 64 channels and operate to block aspiration pressure from reaching the patient's eye in response to detecting conditions indicating possible vacuum surge or vacuum surge.

In this connection it should be noted that one or more sensors 116 may be located within handpiece 50, within main unit 102, and/or incorporated within AVS module 59.

Needle 54 and sleeve 55 located at a distal end of handpiece 50 provide irrigation and aspiration to the eye, as well as transmit vibrations to emulsify lens material. Typically, in some examples, irrigation fluid may flow into eye volume through a region between outer wall of needle 54 and inner wall of sleeve 55. While in some configurations, aspiration channel 64 may flow through needle 54.

The at least one orientation detection unit 60 is configured to determine data on orientation of handpiece 50 and transmit orientation data to one or more processor 118, typically placed in main unit or console 102. Orientation detection unit 60 may include one or more accelerometers, gyroscopic unit, or any other type of orientation sensor. The at least one orientation detection unit 60 may be configured to generate output orientation data indicative on at least pitch orientation of handpiece 50. This is associated with direction of orientation variation, where pitch orientation variation may generally affect height of fluid column that may be formed between the distal end of handpiece 50 and one or more sensors 116. In some examples, orientation detection unit 60 may be configured to generate output orientation data indicative on at least pitch and yaw orientation of handpiece 50. In some further examples, orientation detection unit 60 may be configured to generate output data indicative of pitch, yaw, and roll orientation of handpiece 50.

Generally, handpiece 50 may be electronically coupled with the one or more processors 118 (or PMC as described below) and may provide an interface enabling a physician, scrub nurse, or other operator, to operate the phacoemulsification system and control its operational parameters. The handpiece may include an operation interface in the form of buttons, dials, touchscreen section, foot pedal etc., enabling a physician to provide operation instructions to processor 118. More specifically, an operator, being a surgeon, nurse or technician may control and/or program selected operations using the user interface and one or more input methods such as a button, pedal etc. Certain exemplary configurations of the handpiece are described in U.S. Pat. No. 11,806,465 assigned to the assignee of the present application and incorporated herein by references. Further, as indicated above, the at least one orientation detection unit 60 is configured to provide orientation data and transmit the orientation data to processor 118 to enable the processor to consider the orientation of handpiece 50 in calibration of sensor(s) 116.

Unit 102 may include irrigation module 112, aspiration module 114, driver module 115 and processor 118. As indicated above, unit 102 may in some configurations include one or more sensors 116. Processor 118 is typically associated with a memory and input/output interface, providing a processor and memory circuitry (PMC). Processor, or PMC 118 is operatively coupled with the input/output interface and configured to provide processing necessary for operating system 100 as further described. Processor 118 can be configured to execute several functional modules in accordance with computer readable instructions stored in the memory and/or implemented via one or more computer readable media. Processor 118 may operate irrigation module 112, aspiration module 114, and driver 115 in accordance with one or more operation schemes determined by an operation (e.g., physician or nurse). As indicated above, the operator may determine operation scheme and parameters via user interface including e.g., one or more buttons/pedals as described above.

Phacoemulsification system 100 is configured and operable for performing one or more medical operations, such as cataract operation. The system is further configured for operating in a pre-operation priming and/or tuning mode. In the pre-operation priming and/or tuning mode, phacoemulsification system 100 may operate to prepare the system for operation, typically by flowing fluid through irrigation channel 62 and/or aspiration channel 64 and ensuring selected pressure conditions required for suitable operation of the system. To this end, phacoemulsification system 100 further includes a priming cover (also known as a test chamber) 56 configured to fit on and provide cover to the distal end of handpiece 50, including covering needle 54 and sleeve 55 thereof. Priming cover 56 is connected or connectable with one or more external sensors 80, e.g., pressure sensors, via channel 82. The one or more external sensors 80 is configured to provide sensing data indicative of pressure (e.g., fluid pressure) through priming cover 56 and needle 54 and sleeve 55. The one or more external sensors 80 is connectable to unit 102 to provide output sensing data to the one or more processors 118 thereof. In some examples of the present disclosure, the one or more processors 118 utilize calibration pressure data collected from the one or more external sensors 80 to calibrate pressure data collected by one or more sensors 116 of the system.

Further, while operating in pre-operation priming and/or tuning mode, the one or more processors 118 is configured to utilize orientation data transmitted by the at least one orientation detection unit 60 to adjust pressure output data of the one or more sensors 116 in accordance with orientation of handpiece 50. As indicated above, when the irrigation channel 62 and aspiration channel 64 are filled with fluid, certain amount of fluid may be present between the tip of needle 54 and sleeve 55 and the location of one or more sensors 116. For example, if handpiece 50 is positioned in a horizontal orientation as illustrated in FIG. 1, the capture volume of fluid does not specifically affect the pressure reading. However, when handpiece 50 is held in a vertical position, having the distal end of needle 54 and sleeve 55 pointing upward with respect to gravity, the capture volume of fluid may increase pressure at the location of one or more sensors 116, affecting the pressure reading. On the other hand, if handpiece 50 is held at vertical orientation having the distal end of needle 54 and sleeve 55 pointing downward with respect to gravity, the volume of fluid captured above (with respect to gravity) the one or more sensors 116 may be different and may be associated with volume of fluid within connection line 104 and flexibility/compliance of connection line 104.

Generally, a phacoemulsification system may be used in a cataract procedure. During the procedure, distal end of the handpiece may be directed into a patient's eye through a small incision in the sclera or cornea. The needle of the handpiece may vibrate using piezoelectric vibrating element 52 to emulsify the lens of the eye. The system is further operated to provide irrigation fluid into the eye, and to aspirate the irrigation fluid together with other fluids in the eye and the emulsified lens, forming together eye fluids, to remove the fluids from the eye. Pressure variation within the patient's eye is preferably minimized to avoid collapse of the cornea and maintain eye structure to avoid surgical complications.

In some examples of the present disclosure, the one or more processors 118 may also receive orientation and/or location data indicative of orientation and/or location of handpiece 50, from the at least one orientation detection unit 60. The one or more processors may store the orientation and/or location data, and may process this data to monitor physician actions during the operation.

Additionally, according to some examples of the present disclosure, phacoemulsification system 100 may carry pre-stored computer readable instructions indicative of a priming mode operation. The pre-stored instructions include instructions that when executed by the one or more processors 118, cause the processor to operate irrigation module 112 and aspiration module 114 for preparing the respective irrigation line 106 and aspiration line 108 extending between unit 102 and handpiece 50 to allow fluid flow between the distal end of handpiece 50 and the respective irrigation module 112 and aspiration module 114. The pre-stored instruction also includes instructions to obtain calibration pressure data from the one or more external sensors 80, and to obtain orientation data from the at least one orientation detection unit 60. The calibration pressure data is indicative of pressure detected at the distal end of handpiece 50, and the orientation data is indicative of orientation of handpiece 50. The pre-store instructions, when executed by the one or more processors, cause the one or more processors 118 to use the calibration pressure data and orientation data to calibrate one or more sensors 116 in accordance with pressure at the distal end of handpiece 50.

Connection line 104 may be of a selected length and flexibility to provide maneuverability in position of handpiece 50 and allow a physician to perform the required medical operation. Connection line 104 may include tubing for irrigation and aspiration and additional wiring for communication between handpiece 50 and unit 102. In some examples, as mentioned above, one or more sensors 116 may be placed within unit 102, and configured for collecting sensing data along irrigation channel 62 and/or aspiration channel 64. In such configurations, length, and path of connection line 104, may result in variation between the pressure measured by sensor(s) 116 and actual pressure at the distal end of handpiece 50.

In some examples, connection line 104 may be flexible to minimize length of a portion of the line that is located above the handpiece, when the handpiece is held in various orientations, or to provide selected predetermined length of the connection line 104 above the handpiece. More specifically, connection line 104 may be configured to minimize the length of connection line 104 above handpiece 50, when handpiece 50 is held with the distal end pointing downward. This configuration enables reducing, or setting a predetermined volume of fluid located between the handpiece and a highest point of the connection line 104 with respect to gravity, to thereby enable monitoring of pressure variation associated with fluid accumulated within the connection line at different orientations of the handpiece.

Additionally, as exemplified in FIG. 1, one or more sensors 116 may be placed within the handpiece, or at a selected location along connection line 104. This location of sensor(s) 116 may simplify the structure of the system. However, distance between the one or more sensors 116 and distal end, or tip of needle 54 and sleeve 55 of handpiece 50 may still cause variation between measured pressure and actual pressure at the distal end of the handpiece. Such pressure variation may be associated with the distance from the distal end, as well as due to weight of fluid located within handpiece 50, or within connection line 104 in accordance with orientation of the handpiece. Additionally, in some configurations, tubing compliance issues, associated with tubing between the distal end of handpiece 50 and the one or more sensors 116 may also affect pressure measurements.

More specifically, according to some examples, prior to performing a medical operation, phacoemulsification system 100 is operable in priming and/or tuning mode. While operating in priming and/or tuning mode, the system 100 operates irrigation module 112 and aspiration module 114, for pushing fluid through irrigation line 106 and irrigation channel 62 toward needle 54 and sleeve 55 at the distal end of the handpiece and pulling fluid through aspiration channel 64 and aspiration line 108 toward unit/console 102. Irrigation fluid may be provided to phacoemulsification system 100 via a fluid reservoir (not shown) by either one or more pumps or a gravity fed bottle/bag. This is performed to ensure that irrigation line 106 and irrigation channel 62 are filled with fluid and any air bubbles are removed. The exact configuration of the distal end including tip of needle 54 and the respective sleeve 55 is generally known in the art and may vary between phacoemulsification systems in accordance with medical requirements for different conditions during operation. Generally, sleeve 55 surrounds at least a portion of needle 54 and includes one or more apertures at a side of the sleeve, allowing flow of irrigation fluid around needle 54 and into the patient's eye.

Additionally, system 100 operates aspiration module 114, typically including at least one pump configured to apply vacuum conditions though the aspiration line 108 and aspiration channel 64, via needle 54 to pull the fluid introduced by the irrigation module 112 through the aspiration module 114 and remove any air bubbles in the system. Additionally, according to some examples of the present disclosure, at least one processor 118 operates to obtain pressure data from one or more internal sensors 116 and from one or more external sensors 80 and orientation data from the at least one orientation detection unit 60. The at least one processor further operates to calibrate pressure readout of the one or more pressure sensors 116 in accordance with calibration pressure data obtained from the one or more external sensors 80 and in accordance with orientation of the handpiece 50. The at least one processor 118 may operate to determine a relation, or a function defining a relation between pressure output of the one or more sensors 116 and the pressure data obtained from one or more external sensors 80. For example, in some situations, pressure detected by one or more sensors 116 may be lower (or higher) than pressure detected by one or more external sensors 80 by a fixed pressure difference. In such cases, the determined relation may be determined as $P_{116}=(P_{80}+\Delta P)\times f(\theta)$, where $P_{116}$ is pressure data detected by one or more pressure sensors 116, $P_{80}$ is pressure data detected by one or more external sensors 80, $\Delta P$ is the detected pressure difference, $\theta$ is orientation angle of the handpiece with respect to vertical axis, and $f(\theta)$ is a selected function. In some examples, $f(\theta)$ may be in the form of $A[b+\cos(\theta)]$, $A[b+\cos^2(\theta)]$ or other types of angular dependent functions, indicating a relation between orientation angle and pressure variation. In some other situations, pressure detected by one or more sensors 116 may be lower (or higher) than pressure detected by one or more external sensors 80 by certain ratio $R(\theta)$ that may depend on the orientation angle. In such cases, the determined relation may be of the form $P_{116}=P_{80}\times R(\theta)$, where $P_{116}$ is pressure data detected by one or more pressure sensors 116, $P_{80}$ is pressure data detected by one or more external sensors 80, and $R(\theta)$ is the determined ratio, being smaller or greater than unity and having selected dependency on orientation angle $\theta$. In some situations, the determined relation may be linear, in the form $P_{116}=P_{80}\times R(\theta)+\Delta P\times f(\theta)$. In some other situations, the determined relation may include a quadratic factor or other factors as determined by the one or more processors 118 during calibration.

In some examples, the use of orientation of the handpiece to determine/adjust pressure reading during operation of system 100 in a medical operation such as eye surgery, may allow for simplifying system design. More specifically, the use of orientation detection unit 60, and the respective orientation data may allow for improved detection of IOP, even with sensors 116 that are located further from the distal end of handpiece 50. Flexibility in determining location of pressure sensor 116 may be used to simplify system design and manufacturing, and accordingly the cost of system 100.

After determining the relation between the pressure data measured by the one or more external sensors 80 and one or more sensors 116 and orientation of handpiece 50, the one or more processors 118 may operate to determine a calibration factor, or calibration function, enabling conversion of pressure data determined by one or more sensors 116, orientation angle, and the pressure that is determined by one or more external sensors 80. The at least one processor 118 may operate to store the calibration factor in a respective memory unit, together with instructions on conversion of pressure output from one or more sensors 116 during operation in accordance with the calibration factor. To this end, in some examples of the present disclosure the at least one processor 118 may obtain orientation data from the at least one orientation detection unit 60 during operation and utilizes data on the orientation angle of handpiece 50 for tunning or correcting pressure output data of the one or more sensors 116. Thus, system 100, or the at least one processor 118 thereof may utilize the orientation dependent calibration factor to adjust output data indicative of fluid pressure obtained from the one or more sensors 116 system during operation to provide data on pressure that is adjusted to pressure at the distal end of the handpiece.

The one or more external sensors 80 may be fully external to phacoemulsification system 100, or be a part of the system. In this connection, the one or more externals sensors 80 may be external in the sense of measuring pressure at an external location, i.e., measure pressure at distal end of handpiece 50 via priming cover 56. The one or more external sensors 80 may include any type of sensor capable of detecting pressure variation, including for example, capacitive sensors, strain gauge sensor, piezoelectric sensor, bourdon type sensor, manometer sensor, etc.

Figure 2:
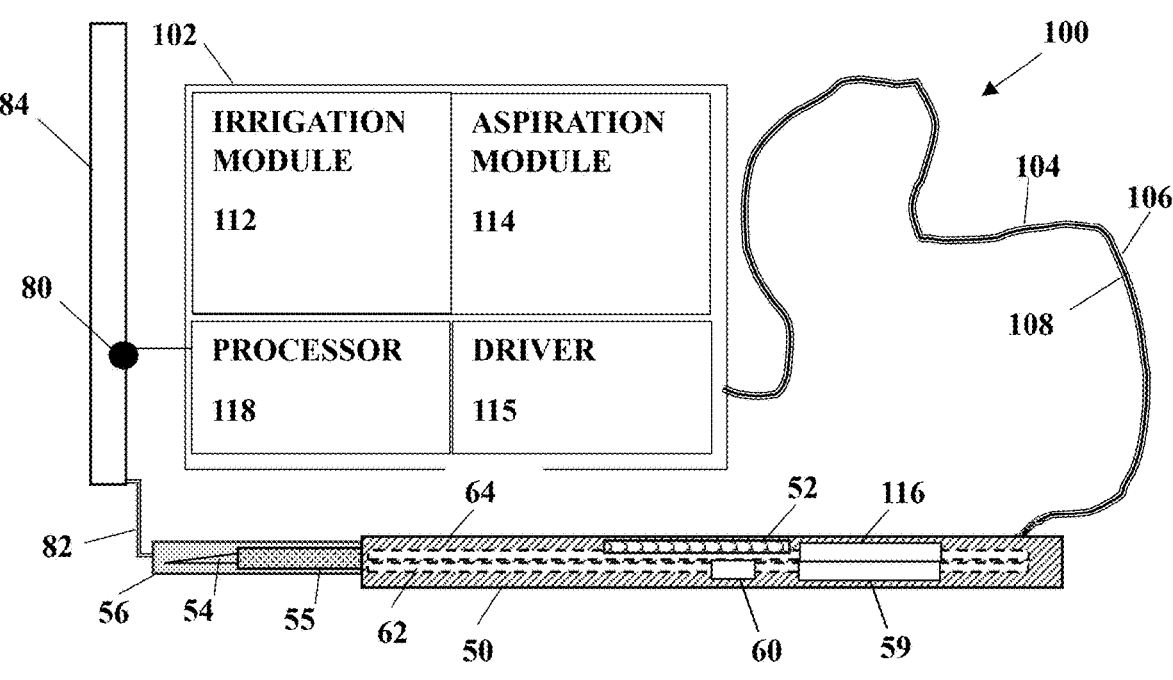
FIG. 2 schematically illustrates another phacoemulsification system utilizing one or more external pressure sensors and a water column according to some examples of the present disclosure.

In this connection, reference is made to FIG. 2 illustrating schematically a phacoemulsification system 100 according to some examples of the present disclosure. The configuration of FIG. 2 is generally similar to that of FIG. 1, except that the one or more external sensors 80 is coupled with a water column 84. More specifically, FIG. 2 exemplifies phacoemulsification system 100 including frame or unit 102 housing an irrigation module 112, aspiration module 114, driver 115 and one or more processors 118, and being connected using a connection line 104 to handpiece 50 including irrigation line 106 and aspiration line 108. Handpiece 50 is exemplified including vibrating (piezoelectric) element 52, pressure sensor 116, AVS module 59, and orientation detection unit, as well as needle 54 and sleeve 55 located at the distal end of the handpiece. Irrigation channel 62 is configured to couple sleeve 55 with irrigation line 106 and aspiration channel 64 is configured to couple needle 54 with aspiration line 108. As indicated above, certain element may be located otherwise than illustrated, for example, pressure sensors 116 and AVS module 59 may be placed along connection line 104 or within frame 102.

Water column 84 provides a relatively simple and reliable pressure measurement. Water column 84 may be associated with one or more sensors 80 configured for determining height of water column 80 and using height data to determine fluid pressure as measured at the priming cover 56. Additionally, or alternatively, one or more sensors 80 may include a capacitive sensor, or any other type of pressure sensor, associated with a diaphragm being in fluid communication with fluid in water column 84.

As indicated above, the one or more external sensors 80, and/or water column 84 when used, may be physically external to the phacoemulsification, coupled with the frame of unit 102, or form an integral part of phacoemulsification system 100. In some examples, where the one or more external sensors 80 and/or water column 84, are integral part of the system, the one or more sensors are external in the meaning that sensors 80 are connected to determine pressure data at the distal end of handpiece 50, through priming cover 56.

Figure 3A:
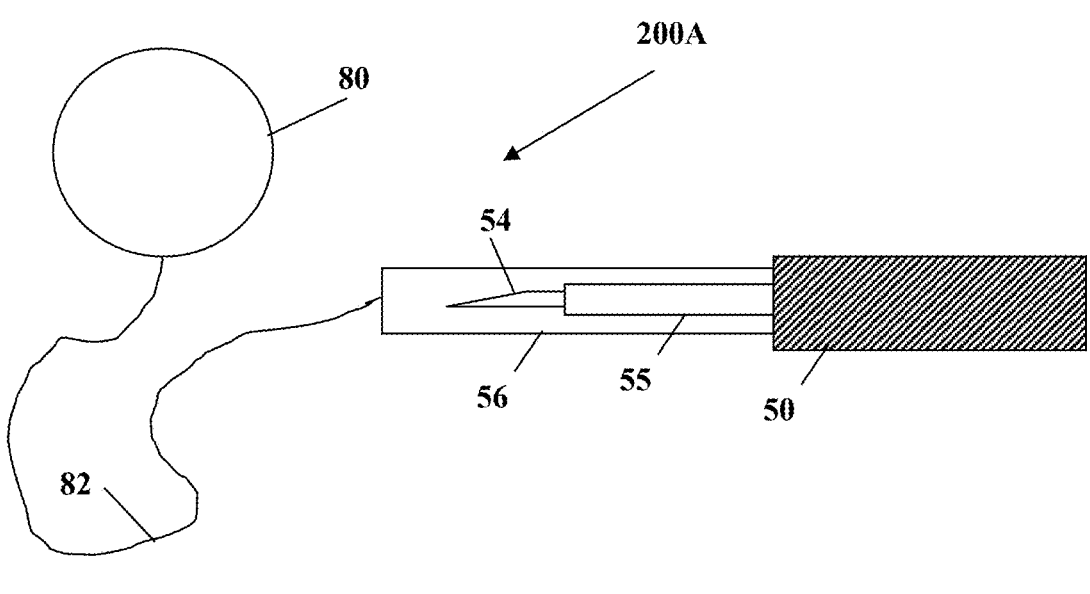
FIGS. 3A to 3C exemplify different orientation of the handpiece while being connected to external pressure sensor.
Figure 3B:
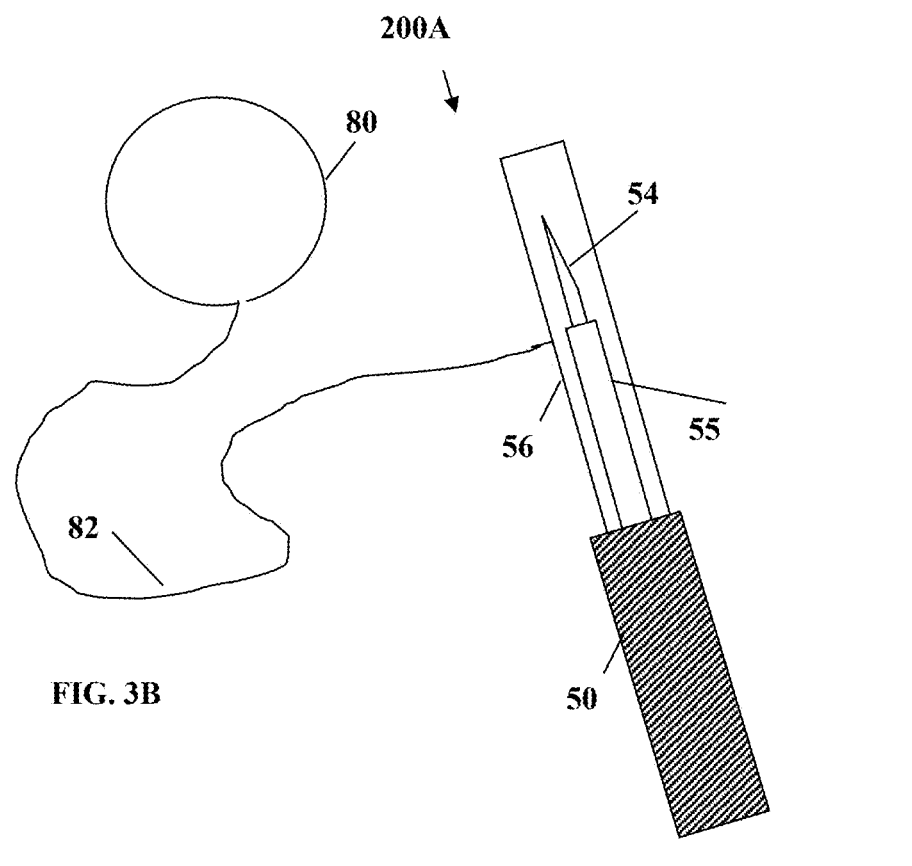
Figure 3C:
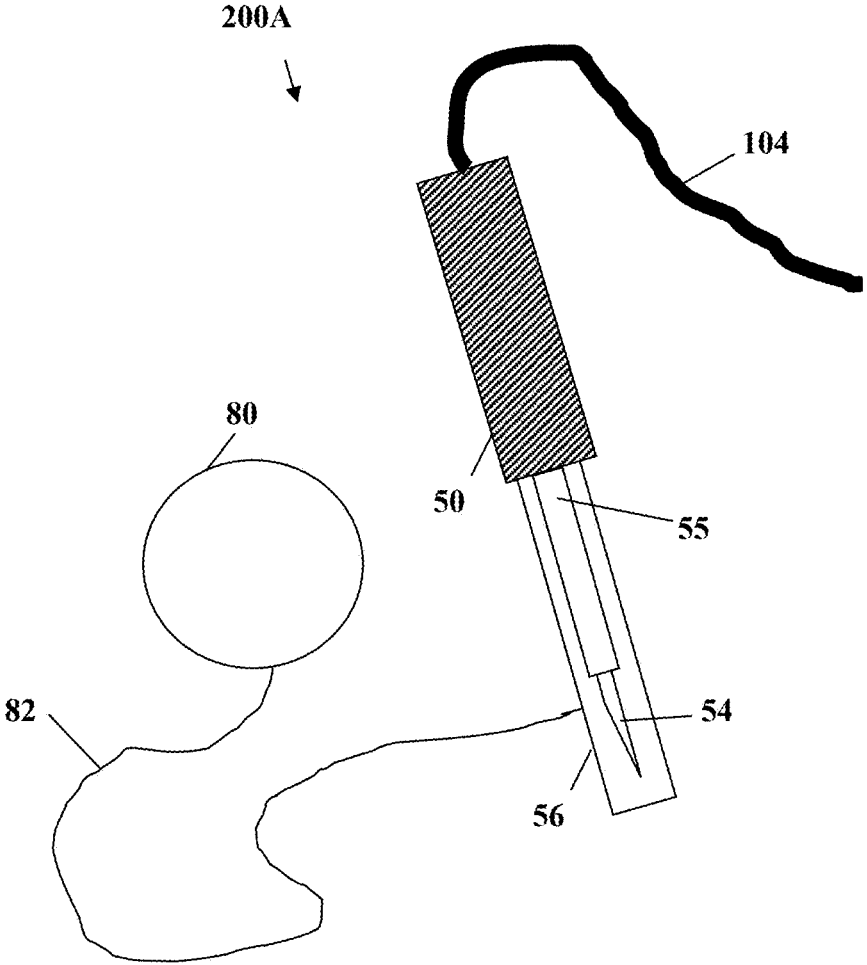

Additionally, priming cover 56, together with at least one or more channels (tubes) 82, connecting the priming cover to the one or more external sensors 80 and/or to water column 84, may be sterilized prior to use. Accordingly, in some examples, a priming kit, including at least a priming cover 56 connected via channel 82 to one or more externals sensors 80 may be used separately from phacoemulsification system 100. This is exemplified in FIGS. 3A to 3C, illustrating external sensor kit 200A according to some examples of the present disclosure while exemplifying variations in orientation of handpiece 50. External sensor kit 200A includes at least a priming cover 56 coupled with one or more pressure sensors 80 via a channel 82.

As shown in FIG. 3A, when handpiece 50 is placed in a horizontal orientation, fluid accumulating within the irrigation channel, that runs along the longitudinal axis of handpiece 50, is dispersed horizontally. Accordingly, the internal one or more sensors of the system 116 collect pressure data indicative of the fluid pressure. In the example of FIG. 3B, the distal end of handpiece 50 is positioned in an upward orientation with respect to gravity. As a result of this orientation, fluid collected between sensor(s) 116 and the distal end of handpiece 50 may act as weight on the fluid at the location of sensor(s) 116 and change the detected pressure. A similar situation is exemplified in FIG. 3C illustrating the distal end of handpiece 50 in a downward orientation with respect to gravity. FIG. 3C further exemplifies a portion of connection line 104 extending from the proximal end of handpiece 50. Is this orientation, the volume of fluid collected between the highest location along line 104 and sensor(s) 116 may vary in accordance with flexibility/compliance of connection line 104. As indicated above, the collected fluid volume may affect the pressure reading by pressing on the fluid located near sensor(s) 116 and varying the pressure thereof.

Figure 4:
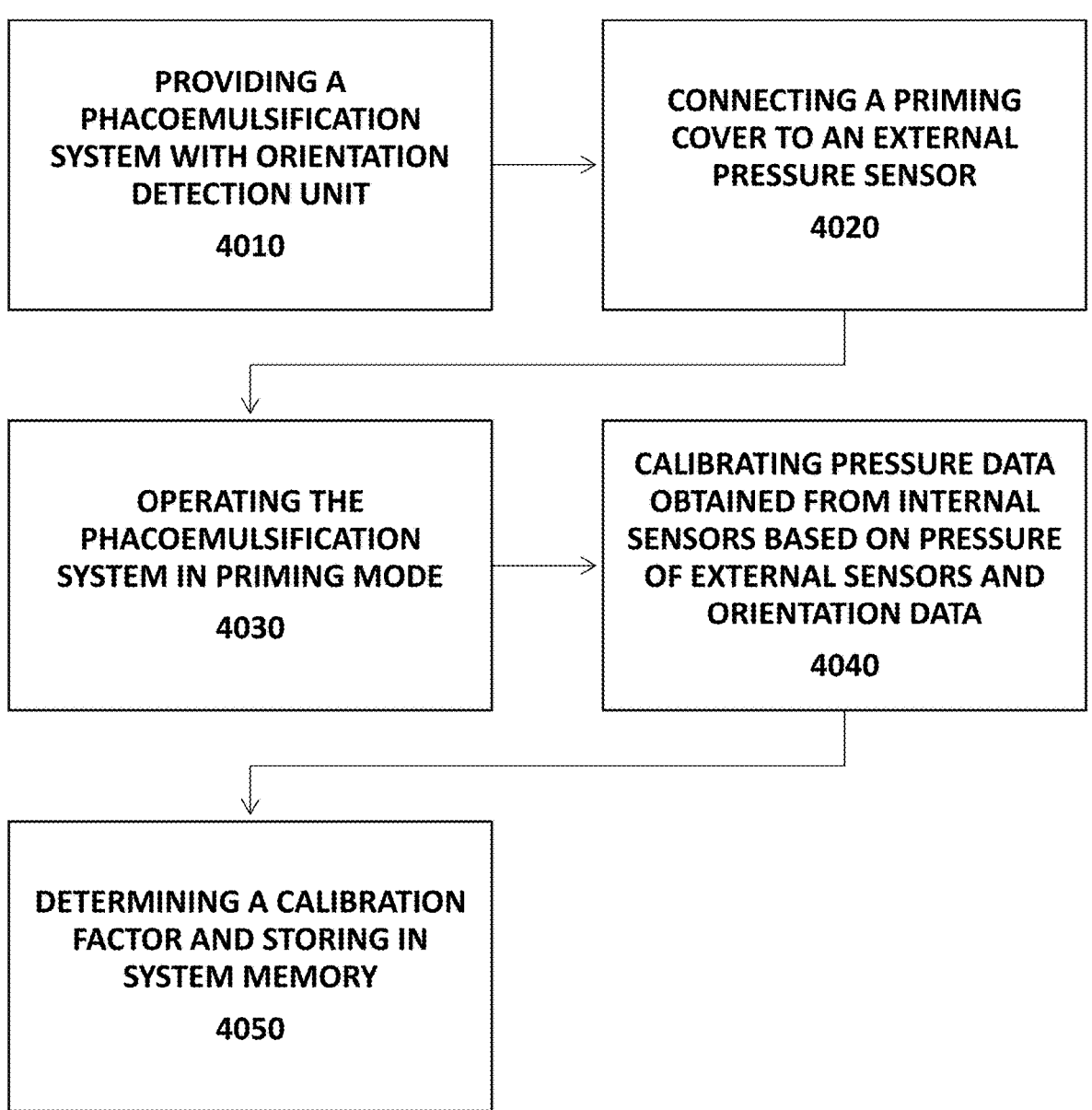
FIG. 4 exemplifies a method for use in priming of a phacoemulsification system according to some examples of the present disclosure.

Further, reference is made to FIG. 4, exemplifying a method for priming a phacoemulsification system. As shown, the method includes providing a phacoemulsification system with at least one orientation detection unit at step 4010. Connecting a priming cover placed on distal end of a handpiece of the phacoemulsification system to one or more external pressure sensors at step 4020. When the one or more external sensor is coupled with the distal end via the priming cover, the method proceeds to operating the phacoemulsification system in a priming and/or tuning mode at step 4030. Operation in priming and/or tuning mode is used prior to operation of the system for a medical procedure, to fill irrigation and/or aspiration channels with fluid (e.g., balanced salt solution), remove air bubbles from the channels, and verify proper operation of the system. Typically, the instructions to an operator include clear indication to maintain the handpiece at rest (in a particular orientation) during priming. The technique of the present disclosure, however, may allow the operator, being physician, surgeon and/or nurse, to hold the handpiece in any orientation, and allow it to be move. Further, the method includes calibrating pressure data obtained from one or more sensors of the system based on calibration pressure data from the one or more external sensors and orientation of handpiece 4040, determining a calibration factor and storing the calibration factor in a memory for use during system operation at step 4050. Allowing the handpiece to be moved during priming may also enable collection of orientation data and respective effect of the orientation data on pressure data collected by the one or more sensors of the phacoemulsification system. As indicated above, the calibration factor may be dependent on orientation of the handpiece. In addition to relaxing conditions during priming, this may enhance accuracy in pressure detection, by adjusting pressure output data to handpiece orientation during the operation and compensating for variation in pressure due to change in orientation of the handpiece.

This method provides for calibrating one or more sensors of the phacoemulsification system using externally detected pressure data and data on orientation of the handpiece. As indicated above, pressure data collected by one or more sensors of the system (e.g., sensors 116 in FIGS. 1 and 2) may vary from the pressure at distal end of the handpiece as a result from pressure and flow variation between the distal end of the handpiece and the sensors, as well as due to variation in orientation of the handpiece. This may be associated with irrigation and/or aspiration channels within the handpiece and/or the connection line (104 in FIGS. 1 and 2) and the weight of fluid within the channels. Calibration of the one or more sensors is directed to align pressure data obtained by the one or more sensors of the system during operation of the system with actual pressure at the distal end of the handpiece. As indicated above, while operating for priming the phacoemulsification system, the technique of the present disclosure utilizes pressure data collected by the system and external sensors and orientation data indicative of orientation of the handpiece, to calibrate the one or more sensors of the system. In some examples, the technique may also utilize additional parameters such as irrigation flow rate during priming, to enhance calibration. The calibration process may be used to determine a relation, or calibration factor, which is stored in memory unit of the system. Further, during operation, the one or more processors of the phacoemulsification system may use the stored calibration factor to convert pressure data collected by the system's sensors and determine actual pressure conditions at the distal end of the handpiece.

As indicated above, in some examples, action 4020 may include connecting a phacoemulsification system with a kit including priming cover as described in FIGS. 3A to 3C above and using one or more external sensors for calibrating the system sensors with the pressure data for different orientations of the handpiece as described herein.

FIG. 5 shows a further method for use in priming of a phacoemulsification system according to some examples of the present disclosure. In this example, the method includes coupling one or more external pressure sensors with priming cover of the phacoemulsification system in step S010 and operating the phacoemulsification system in a priming mode in step S020. Operating in the priming mode may include priming irrigation and aspiration channels so that the air (bubbles) in the irrigation and aspiration channels is removed in step S030. Additionally, during the priming mode, the method includes operating the system (irrigation and aspiration modules) to obtain pressure data from the one or more system sensors at step S040 and to obtain calibration pressure data from the external pressure sensors at step S050. Additionally, the method includes obtaining orientation data indicative of handpiece orientation in step S060. Generally, in some examples, actions 5040, 5050 and 5060 may be performed in parallel or any selected order and are not necessarily in the order illustrated in FIG. 5. As indicated above, the orientation data includes at least pitch variation of the handpiece, associated with upward or downward orientation angle of the distal end of the handpiece with respect to gravity. The system may operate the irrigation module for providing irrigation fluid in one or more different selected flow rates. And to operate the aspiration module for generating selected vacuum conditions, to provide variations in pressure conditions. Additionally, in accordance with operator instructions, the handpiece may be moved providing variation in orientation data during priming. In some examples, the operator instructions may include instructions on holding and moving the handpiece in surgery mimicking fashion to enhance accuracy of pressure calibration. Further, the method may include determining a relation between system pressure, collected by system sensors (e.g., 116 in FIGS. 1 and 2) and calibration pressure collected by external sensors 5070 and determining variations of the so-determined relation for different orientations of the handpiece in step S080. As indicated above, the pressure relation may be in the form of a function describing variation between the different pressure measurements and at least one orientation angle (e.g., pitch angle). In some examples, the relation may be in the form of a lookup table specifying the calibration pressure measured for different operation conditions such as different flow rates and aspiration levels, and the pressure measured by the system sensors in the same operating conditions. Using the determined relation, the method may operate to determine a calibration factor and store the calibration factor for later use, e.g., in a memory unit at step at step S090. The calibration factor may be a one- two- or multi-dimensional factor describing adjustment to pressure data collected by the system sensors to what would be the pressure if measured at the distal end of the handpiece based on at least the orientation of the handpiece. In some examples, the calibration factor may depend on system pressure data. In some examples, the calibration factor may depend on one or more additional operational characteristics such as irrigation rate, aspiration level, etc.

After priming, the phacoemulsification system may be ready for use in a medical procedure. During the medical procedure, the method may include obtaining pressure data from the system sensors and converting the pressure data in accordance with the stored calibration factor at step S100. This provides output pressure data calibrated to pressure that would be measured at the distal end of the handpiece, where the system interfaces with a patient's eye. Accordingly, the method of the present disclosure may be used to enhance accuracy and reproducibility of pressure data during a medical operation using a phacoemulsification system, to eliminate, or at least significantly reduce complications during the medical procedure.

The present disclosure thus provides for a phacoemulsification system and a method for use in priming of a phacoemulsification system. The present technique utilizes at least one orientation detection unit for adjusting pressure measurements within the system based on the variations/changes in orientation of the handpiece.

EXAMPLES

Example 1: A phacoemulsification system (100) comprising:
- (a) a handpiece (50) comprising a piezoelectric element (52) and a distal end comprising a needle (54) and a sleeve (55), wherein the distal end is configured to be inserted into an eye and to be vibrated by the piezoelectric element (52) to emulsify a lens of the eye;
- (b) an irrigation module (112) configured to supply a flow of irrigation fluid into the eye, the irrigation module (112) is configured to be coupled with an irrigation channel (62) of the handpiece (50) via an irrigation line (104) so as to enable flow of irrigation fluid therethrough;
- (c) an aspiration module (114) configured for aspirating eye fluid, the aspiration module (114) module is configured to be coupled with an aspiration channel (64) of the handpiece (50) via an aspiration line (108) so as to enable flow of an eye fluid therethrough;
- (d) a priming cover (56) configured to fit over the distal end of the handpiece (50) during a priming process;
- (e) one or more external pressure sensors (80) configured to be coupled with the priming cover (56);
- (f) one or more sensors (116) coupled with at least one of the irrigation channel (62), the irrigation line (106), the aspiration channel (64), and the aspiration line (108), and configured to monitor at least one of an irrigation pressure in the irrigation channel (62), an irrigation pressure in the irrigation line (106), an aspiration pressure in the aspiration channel (64), and an aspiration pressure in the aspiration line (108); and
- (g) one or more processors (118) configured, for operating a priming process including:
- operating the irrigation module (112) to fill the irrigation channel (62) and the irrigation line (106) with irrigation fluid so that the irrigation channel (62) and the irrigation line (106) are free from air and irrigation fluid fills the priming cover:
    - wherein the handpiece (50) further comprises at least one orientation detection unit (60); and wherein the one or more processors (118) being further configured for obtaining calibration pressure data from the one or more external pressure sensors (80) and orientation data from the at least one orientation detection unit (60) for calibrating pressure output data of the one or more sensors (116) coupled with the irrigation channel or the aspiration channel based on the calibration pressure data and orientation of the handpiece (50).

Example 2: The phacoemulsification system (100) of example 1, wherein the at least one orientation detection unit (60) comprises at least one accelerometer.

Example 3: The phacoemulsification system (100) of example 1 or 2, wherein the at least one orientation detection unit (60) comprises an arrangement of three or more accelerometers.

Example 4: The phacoemulsification system (100) of any one of examples 1 to 3, wherein the at least one orientation detection unit (60) comprises at least one gyroscope.

Example 5: The phacoemulsification system (100) of any one of examples 1 to 4, wherein the at least one orientation detection unit (60) is configured to generate orientation data indicative of at least pitch angle of the handpiece (50).

Example 6: The phacoemulsification system (100) of example 5, wherein the phacoemulsification system (100) further comprises a water column, wherein the one or more external pressure sensors (80) are coupled with the water column.

Example 7: The phacoemulsification system (100) of any one of examples 1 to 6, wherein the one or more external pressure sensors (80) comprises at least one capacitive pressure sensor.

Example 8: The phacoemulsification system (100) of any one of examples 1 to 7, wherein the one or more processors (118) is adapted for determining a calibration factor defining a relation between the calibration pressure data obtained from the one or more external pressure sensors (80), pressure data of the one or more sensors (116), and orientation of the handpiece (50).

Example 9: The phacoemulsification system (100) of any one of examples 1 to 8, wherein said one or more processors (118) is configured to utilize said calibration factor for adjusting output data indicative of fluid pressure of said phacoemulsification system (100) and orientation of the handpiece (50) during operation.

Example 10: A method for use in priming a phacoemulsification system, the method comprising:

(a) providing at least one external pressure sensor (80) to be coupled with a working end of a handpiece (50) of said phacoemulsification system (4010);

(b) operating said phacoemulsification system for priming (4030) thereof while:

i) obtaining external pressure data (5050) from at least one external pressure sensor (80); and ii) obtaining handpiece orientation data (5060) from at least one orientation detection unit (60); and calibrating pressure data (4040) of one or more sensors of the phacoemulsification system in accordance with the external pressure data and orientation of the handpiece.

Example 11: The method of example 10, wherein said providing at least one external pressure sensor (80) coupled with a working end of said handpiece (50) comprises coupling said at least one pressure sensor with a priming cover (5020) configured for covering said working end of said handpiece (50), thereby providing said at least one external pressure sensor (80) to determine fluid pressure at said working end of said handpiece (50).

Example 12: The method of example 10 or 11, wherein the orientation detection unit (60) comprises at least one accelerometer.

Example 13: The method of any one of examples 10 to 12, wherein the orientation detection unit (60) comprises at least one gyroscope.

Example 14: The method of any one of examples 10 to 13, wherein obtaining handpiece orientation data comprises obtaining at least pitch angular orientation of the handpiece (50).

Example 15: The method of any one of examples 10 to 14, wherein said obtaining handpiece orientation data (5060) comprises obtaining handpiece orientation in two or more different pitch orientations of the handpiece (50).

Example 16: The method of any one of examples 10 to 15, wherein said calibrating (4040) comprises determining a relation (5070, 5080) between output data indicative of fluid pressure of said phacoemulsification system and pressure data of said at least one pressure sensor (116), for one or more different orientation angles of the handpiece (50).

Example 17: The method of any one of examples 10 to 16, further comprising utilizing the relation and determining an orientation dependent calibration factor (5100).

Example 18: The method of example 17, further comprising, obtaining handpiece orientation data during operation of the phacoemulsification system, and using the calibration factor for adjusting output data indicative of fluid pressure of said phacoemulsification system in accordance with handpiece orientation (5100).

Example 19: A software program product, embedded in a non-transitory computer readable medium, comprising computer readable instructions that when executed by one or more processors cause the processor to operate a phacoemulsification system in a priming mode, comprising: receiving handpiece orientation data from an orientation detection unit, receiving input handpiece pressure data from at least one external pressure sensor, and receiving system pressure data from one or more sensors of said phacoemulsification system, processing the handpiece pressure data and the system pressure data for one or more different handpiece orientation angles and determining a calibration factor defining a relation between the handpiece pressure data and the system pressure data for the one or more handpiece orientation angles, and calibrating the one or more sensors of said phacoemulsification system in accordance with the calibration factor.

Example 20: The software product of example 19, comprising computer readable instructions for determining a calibration factor indicative of a relation between pressure data of said phacoemulsification system and pressure data of said at least one external pressure sensor, for one or more different orientation angles of the handpiece, and to store said calibration factor is a storage utility.

Example 21: The software product of example 19 or 20, further comprising computer readable instructions for obtaining handpiece orientation data and adjusting pressure output data of said phacoemulsification system in accordance with said calibration factor stored in a storage utility and handpiece orientation during operation.

It is to be noted that the various features described in the various examples can be combined according to all possible technical combinations.

It is to be understood that the invention is not limited in its application to the details set forth in the description contained herein or illustrated in the drawings. The invention is capable of other examples and of being practiced and carried out in various ways. Hence, it is to be understood that the phraseology and terminology employed herein are for the purpose of description and should not be regarded as limiting. As such, those skilled in the art will appreciate that the conception upon which this disclosure is based can readily be utilized as a basis for designing other structures, methods, and systems for carrying out the several purposes of the presently disclosed subject matter.

Those skilled in the art will readily appreciate that various modifications and changes can be applied to the examples of the invention as hereinbefore described without departing from its scope, defined in and by the appended claims.

The invention claimed is:

1. A phacoemulsification system comprising:

(a) a handpiece comprising a piezoelectric element and a distal end comprising a needle and a sleeve, wherein the distal end is configured to be inserted into an eye and to be vibrated by the piezoelectric element to emulsify a lens of the eye;

(b) an irrigation module configured to supply a flow of irrigation fluid into the eye, the irrigation module is configured to be coupled with an irrigation channel of the handpiece via an irrigation line so as to enable flow of irrigation fluid therethrough;

(c) an aspiration module configured for aspirating eye fluid, the aspiration module is configured to be coupled with an aspiration channel of the handpiece via an aspiration line so as to enable flow of an eye fluid therethrough;

(d) a priming cover configured to fit over the distal end of the handpiece during a priming process;

(e) one or more external pressure sensors configured to be coupled with the priming cover;

(f) one or more sensors coupled with at least one of the irrigation channel, the irrigation line, the aspiration channel, and the aspiration line, and configured to monitor at least one of an irrigation pressure in the irrigation channel, an irrigation pressure in the irrigation line, an aspiration pressure in the aspiration channel, and an aspiration pressure in the aspiration line; and (g) one or more processors configured for operating a priming process including:

operating the irrigation module to fill the irrigation channel and the irrigation line with irrigation fluid so that the irrigation channel and the irrigation line are free from air and irrigation fluid fills the priming cover;

wherein the handpiece further comprises at least one orientation detection unit; and wherein the one or more processors being further configured for obtaining calibration pressure data from the one or more external pressure sensors and orientation data from the at least one orientation detection unit for calibrating pressure output data of the one or more sensors coupled with the irrigation channel, irrigation line, the aspiration channel, or aspiration line based on the calibration pressure data and orientation of the handpiece.

2. The phacoemulsification system of claim 1, wherein the at least one orientation detection unit comprises at least one accelerometer.

3. The phacoemulsification system of claim 1, wherein the at least one orientation detection unit comprises an arrangement of three or more accelerometers.

4. The phacoemulsification system of claim 1, wherein the at least one orientation detection unit comprises at least one gyroscope.

5. The phacoemulsification system of claim 1, wherein the at least one orientation detection unit is configured to generate orientation data indicative of at least pitch angle of the handpiece.

6. The phacoemulsification system of claim 1, wherein the phacoemulsification system further comprises a water column, wherein the one or more external pressure sensors are coupled with the water column.

7. The phacoemulsification system of claim 1, wherein the one or more external pressure sensors comprises at least one capacitive pressure sensor.

8. The phacoemulsification system of claim 1, wherein the one or more processors is adapted for determining a calibration factor defining a relation between the calibration pressure data obtained from the one or more external pressure sensors, pressure data of the one or more sensors, and orientation of the handpiece.

9. The phacoemulsification system of claim 8, wherein said one or more processors is configured to utilize said calibration factor for adjusting output data indicative of fluid pressure of said phacoemulsification system during operation and orientation of the handpiece.

* * * * *